US011938314B2

(12) United States Patent
Burns, IV et al.

(10) Patent No.: US 11,938,314 B2
(45) Date of Patent: Mar. 26, 2024

(54) METHOD OF MANUFACTURING AN IMPLANTABLE NEURAL ELECTRODE INTERFACE PLATFORM

(71) Applicant: The Charles Stark Draper Laboratory, Inc., Cambridge, MA (US)

(72) Inventors: John Burns, IV, Cambridge, MA (US); Julianne Grainger, Boston, MA (US); Bryan McLaughlin, Cambridge, MA (US); Tirunelveli S. Sriram, Acton, MA (US); John Lachapelle, Princeton, MA (US)

(73) Assignee: The Charles Stark Draper Laboratory, Inc., Cambridge, MA (US)

(*) Notice: Subject to any disclaimer, the term of this patent is extended or adjusted under 35 U.S.C. 154(b) by 752 days.

(21) Appl. No.: 16/921,486

(22) Filed: Jul. 6, 2020

(65) Prior Publication Data
US 2021/0121687 A1    Apr. 29, 2021

Related U.S. Application Data

(63) Continuation of application No. 15/439,419, filed on Feb. 22, 2017, now abandoned.
(Continued)

(51) Int. Cl.
*A61N 1/05* (2006.01)
*A61B 5/00* (2006.01)
(Continued)

(52) U.S. Cl.
CPC .......... *A61N 1/0551* (2013.01); *A61B 5/4041* (2013.01); *A61B 5/4893* (2013.01);
(Continued)

(58) Field of Classification Search
CPC .......... A61N 1/0551; A61N 1/02; A61N 1/05; A61N 1/0534; A61N 1/0539;
(Continued)

(56) References Cited

U.S. PATENT DOCUMENTS 3,244,174 A    4/1966 Wesbey
4,557,887 A    12/1985 Ona et al.
(Continued)

FOREIGN PATENT DOCUMENTS

JP    2007-167636 A    7/2007
JP    2008-136684 A    6/2008
(Continued)

OTHER PUBLICATIONS

International Search Report and Written Opinion dated Jul. 27, 2017 in PCT Application No. PCT/US2017/018875.
(Continued)

*Primary Examiner* — Alonzo Chambliss
(74) *Attorney, Agent, or Firm* — McDermott Will & Emery LLP

(57) ABSTRACT

The present disclosure discusses a method of manufacturing an implantable neural electrode. The method includes cutting a metal layer to form a plurality of electrode sites, contact pads and metal traces connecting the electrode sites to the contact pads. A first silicone layer including a mesh is formed and coupled to the metal layer. A second silicone layer is formed and laminated to the first silicone layer coupled with the metal layer. Holes are formed in the first or second silicone layer exposing the contact pads and electrode sites. Wires are welded to the exposed contact pads and a third layer of silicone is overmolded over the contact pads and wires.

20 Claims, 7 Drawing Sheets

Related U.S. Application Data

(60) Provisional application No. 62/298,272, filed on Feb. 22, 2016.

(51) Int. Cl.
| | | |
|---|---|---|
| *A61N 1/02* | (2006.01) | |
| *A61N 1/04* | (2006.01) | |
| *A61N 1/36* | (2006.01) | |
| *A61B 5/24* | (2021.01) | |
| *A61B 18/00* | (2006.01) | |

(52) U.S. Cl.
CPC .............. *A61B 5/6877* (2013.01); *A61N 1/02* (2013.01); *A61N 1/048* (2013.01); *A61N 1/05* (2013.01); *A61N 1/0529* (2013.01); *A61N 1/0534* (2013.01); *A61N 1/0539* (2013.01); *A61N 1/36185* (2013.01); *A61B 5/24* (2021.01); *A61B 2018/00434* (2013.01); *A61B 2562/125* (2013.01); *A61N 1/0492* (2013.01)

(58) Field of Classification Search
CPC .... A61N 1/0529; A61N 1/04; A61N 1/36185; A61N 1/0492; A61N 1/048; A61B 2018/00434; A61B 2562/125; A61B 5/4041; A61B 5/6877; A61B 5/4893
See application file for complete search history.

(56) References Cited

U.S. PATENT DOCUMENTS

| | | | |
|---|---|---|---|
| 4,969,468 | A | 11/1990 | Byers |
| 7,212,851 | B2 | 5/2007 | Donoghue |
| 7,467,003 | B2 | 12/2008 | Brister |
| 7,877,866 | B1 | 2/2011 | Greenberg |
| 7,937,153 | B2 | 5/2011 | Zhou et al. |
| 7,972,688 | B2 | 7/2011 | Letts |
| 8,453,390 | B2 | 6/2013 | Letts |
| 8,700,114 | B2 | 4/2014 | Gottlieb |
| 9,215,995 | B2 | 12/2015 | Gottlieb |
| 9,795,326 | B2 | 10/2017 | Hoss |
| 10,052,476 | B2 | 8/2018 | Seymour |
| 10,219,384 | B2 | 2/2019 | Stahr |
| 11,523,763 | B2 * | 12/2022 | Wendel-Mitoraj ..... A61B 5/291 |
| 2001/0042291 | A1 | 11/2001 | Esashi |
| 2002/0032374 | A1 | 3/2002 | Holker et al. |
| 2002/0111658 | A1 | 8/2002 | Greenberg |
| 2003/0045919 | A1 | 3/2003 | Swoyer |
| 2003/0195601 | A1 | 10/2003 | Hung |
| 2003/0233134 | A1 | 12/2003 | Greenberg |
| 2004/0082875 | A1 | 4/2004 | Donoghue |
| 2004/0154163 | A1 | 8/2004 | Miyazaki |
| 2005/0142163 | A1 | 6/2005 | Hunter |
| 2005/0210789 | A1 | 9/2005 | Anghel |
| 2006/0204717 | A1 | 9/2006 | Deininger et al. |
| 2006/0225274 | A1 | 10/2006 | Greenberg |
| 2006/0264897 | A1 | 11/2006 | Lobl |
| 2007/0282411 | A1 | 12/2007 | Franz |
| 2007/0293749 | A1 | 12/2007 | Zhou |
| 2008/0027524 | A1 | 1/2008 | Maschino |
| 2008/0046051 | A1 | 2/2008 | Skubitz |
| 2008/0086107 | A1 | 4/2008 | Roschak |
| 2008/0191335 | A1 | 8/2008 | Yang |
| 2008/0299875 | A1 | 12/2008 | Duescher |
| 2009/0025961 | A1 | 1/2009 | Kanemaru |
| 2010/0003904 | A1 | 1/2010 | Duescher |
| 2010/0134951 | A1 | 6/2010 | Brendel |
| 2011/0092842 | A1 | 4/2011 | Decaria |
| 2011/0092870 | A1 | 4/2011 | Jarrell |
| 2011/0093052 | A1 | 4/2011 | Anderson |
| 2011/0257623 | A1 | 10/2011 | Marshall |
| 2012/0319150 | A1 | 12/2012 | Shimomura |
| 2013/0008026 | A1 | 1/2013 | Walter |
| 2013/0053935 | A1 | 2/2013 | Swanson |
| 2013/0144145 | A1 * | 6/2013 | Meng ....................... A61B 5/24 600/377 |
| 2013/0150940 | A1 | 6/2013 | Wilson et al. |
| 2013/0187190 | A1 | 7/2013 | Muramatsu |
| 2013/0192880 | A1 | 8/2013 | Nakanishi |
| 2013/0223034 | A1 | 8/2013 | Rathburn |
| 2013/0313130 | A1 | 11/2013 | Little |
| 2015/0157862 | A1 | 6/2015 | Greenberg et al. |
| 2015/0272737 | A1 | 10/2015 | Dale |
| 2016/0059016 | A1 | 3/2016 | Mercanzini |
| 2016/0355951 | A1 | 12/2016 | Pham |
| 2018/0001081 | A1 | 1/2018 | Minev |

FOREIGN PATENT DOCUMENTS

| | | |
|---|---|---|
| JP | 2009-522015 A | 6/2009 |
| WO | 2011071538 A2 | 6/2011 |
| WO | 2012140262 A1 | 10/2012 |
| WO | 2014157550 A1 | 10/2014 |
| WO | 2015030734 A1 | 3/2015 |
| WO | WO-2017147151 A1 * | 8/2017 ........... A61N 1/0529 |

OTHER PUBLICATIONS

Office Action dated Sep. 13, 2019 in U.S. Appl. No. 15/439,419.
Notice of Allowance dated Apr. 7, 2020 in U.S. Appl. No. 15/439,419.
Office Action dated Oct. 28, 2020 in Japanese Patent Application No. 2018-544167, and English translation hereof.

* cited by examiner

METHOD OF MANUFACTURING AN IMPLANTABLE NEURAL ELECTRODE INTERFACE PLATFORM

RELATED APPLICATIONS

The present application is a continuation of U.S. patent application Ser. No. 15/439,419 filed on Feb. 22, 2017, and titled "METHOD OF MANUFACTURING AN IMPLANTABLE NEURAL ELECTRODE INTERFACE PLATFORM," which claims priority to the U.S. Provisional Application No. 62/298,272 filed on Feb. 22, 2016, and titled "LONGITUDINAL INTRA-FASCICULAR ELECTRODE," which is herein incorporated by reference in its entirety.

BACKGROUND

Peripheral nerves are the nerves outside the central nervous system (e.g., the brain and spinal cord). They serve as a relay, connecting the central nervous system to the limbs and organs.

Peripheral and cortical nerve stimulation are increasingly popular disease treatments. These techniques function by delivering an electrical stimulation pulse to a targeted area in order to create a neural response. Peripheral nerve stimulation has been used to treat chronic pain and migraines. Cortical neural stimulation can be used to treat Parkinson's disease and depression.

SUMMARY OF THE DISCLOSURE

According to one aspect of the disclosure, a method of manufacturing an implantable neural electrode interface platform may include cutting a metal layer to form a plurality of electrode sites, contact pads and metal traces. The metal layer is between about 5 µm and about 25 µm thick. The metal traces connect one or more electrode sites to one or more contact pads. A first silicone layer is formed by knife-coating a polymer mesh with silicone and cured. The first silicone layer is between about 50 µm and about 100 µm thick. The metal layer is coupled to the first silicone layer. A second silicone layer is formed by calendaring silicone to a thickness between about 50 µm and about 100 µm. The first silicone layer is laminated to the second silicone layer. The metal layer is positioned between the first silicone layer and the second silicone layer. A first set of holes are formed in the first or second silicone layers to expose one or more electrode sites. A second set of holes are formed in the first or second silicone layer to expose one or more contact pads in the metal layer. Wires are welded to the exposed contact pads. A third silicone layer is overmolded over the contact pads and a portion of the wires.

In some implementations, a release tape is applied to the metal layer before cutting the metal layer. The release tape may be removed from the metal layer after coupling the cut metal layer to the first silicone layer. The release tape can be removed by heating the release tape, dissolving the release tape in a solvent or exposing the release tape to ultraviolet light.

In some implementations, the metal layer is cleaned with oxygen plasma before laminating the first silicone layer to the second silicone layer. A primer is deposited on the metal layer after cleaning the metal layer with oxygen plasma. In some implementations, laser ablation is used to cut the metal layer and form the first and second sets of holes. A picosecond pulsed laser may be used for the laser ablation.

In some implementations, the mesh includes nylon, polyamide, or polyester fibers. The mesh may include an open area between 40% and 50% of the total area of the mesh. Each fiber of the mesh may have a diameter between about 30 µm and about 50 µm. The mesh fibers may be spaced about 60 µm and about 70 µm apart. The mesh may be between about 40 µm and 50 µm thick. In some implementations, forming the first silicone layer comprises knife-coating the mesh such that the first silicone layer is between about 60 µm and about 90 µm thick and forming the second silicone layer comprises calendaring the second layer of silicone to be between about 60 µm and about 90 µm thick. In some implementations, forming the first silicone layer comprises knife-coating the mesh such that the first silicone layer is between about 70 µm and about 80 µm thick and forming the second silicone layer comprises calendaring the second silicone layer to be between about 70 µm and about 80 µm thick.

In some implementations, resistance welding or laser welding may be used for the welding the wires to the exposed contact pads.

In some implementations, the overmolding achieves a gradual transition between the first or second silicone layer and the third silicone layer.

In some implementations, the first and second sets of holes are both formed in the first silicone layer. In other implementations, the first and second sets of holes are both formed in the second silicone layer. In some implementations, the first set of holes may be formed in a different layer of silicone than the layer of silicone in which the second set of holes is formed.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description of the invention.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present disclosure discusses electrodes and the manufacture thereof. The electrodes are configured to be implanted within (or adjacent to) neural tissue, such as a peripheral nerve. The electrodes are then secured to the nerve fascicle to form an interface between the nerve fibers of the nerve fascicle and a neural stimulator or recording device. The electrodes include a metal layer laminated between adhesive silicone layers. One or more of the silicone layers can include a mesh layer for improved handling and structural integrity. The electrodes can also include a detachable needle that enables insertion of the electrode directly into a nerve fascicle, bundle of nerve fibers, or other tissue. The electrode's insertion into a nerve fiber enables stimulation of the central regions of a nerve.

Figure 1:
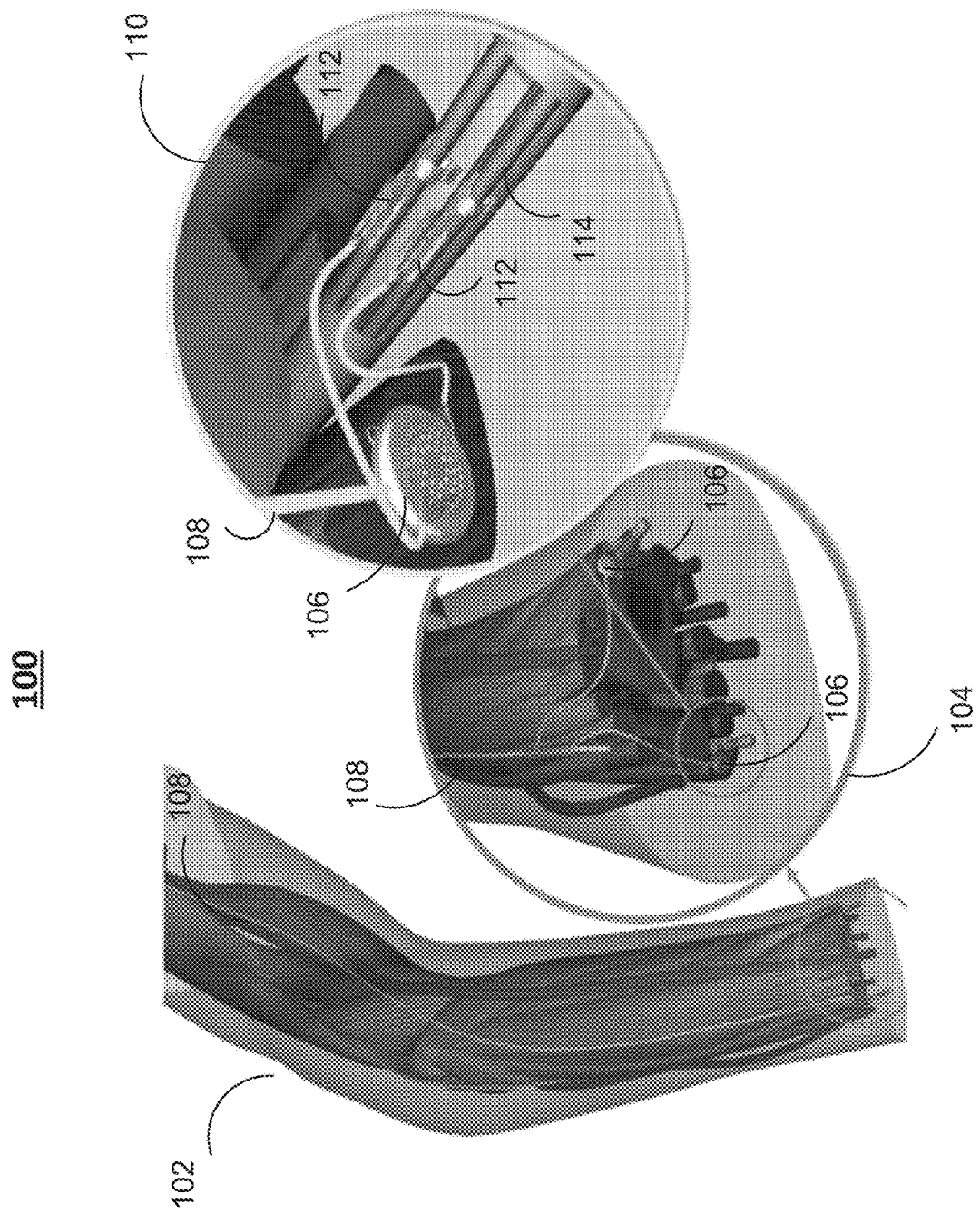
FIG. 1 illustrates a system for peripheral nerve stimulation and recording.

FIG. 1 illustrates a system 100 for peripheral nerve stimulation and recording. While the system 100 can be implanted anywhere in the body, FIG. 1 illustrates the system 100 implanted into the right arm 102 of a patient. The enlarged portion 104 illustrates that two satellites 106 are coupled to a controller hub via a connector 108. The second enlarged portion 110 illustrates that two electrodes 112 are coupled one of the satellites 106. Each of the electrodes 112 are coupled to a peripheral nerve fascicle 114 in the wrist of the arm 102.

As an overview of the system architecture, The system 100 includes a central controller hub (not illustrated) that is implanted into central location, such as in a surgically created sub-dermal pocket in the upper arm or chest. The satellites 106 are coupled to the controller hub and implanted near the regions of interest. The satellites 106 interface with the electrodes 112. Power is provided to the satellites 106 and electrodes 112 by the controller hub. The satellites 106 enable the electrodes 112 to be configured in real-time for recording or stimulation. The satellites 106 also include a neural amplifier with an embedded analog to digital converter that enables recording and digital transmission of neural signals captured by the electrodes 112. The hub or satellite 106 includes stimulation channels for stimulating target tissue via the electrodes 112, one or more processors for adaptive closed-loop control, bidirectional wireless data telemetry for communication with an external base station, and a wirelessly rechargeable lithium battery for power.

The system 100 includes one or more electrodes 112 coupled to each of the satellites 106. The electrodes 112 provide the interface between the system 100 and the patient. The electrodes 112 are configured to be directly secured to a patient's nerve fascicle 114 or other tissue. The electrode 112 includes a plurality of electrode sites along a rostrum. The rostrum is an elongated extension that projects from the body of the electrode 112. In some implementations, the rostrum is configured for implantation through a nerve fascicle to record from (and/or stimulate) one or more of the nerve fibers within the nerve fascicle. The electrode 112 is described further in relation to FIGS. 4A-4K and FIGS. 5A-5D.

Figure 2:
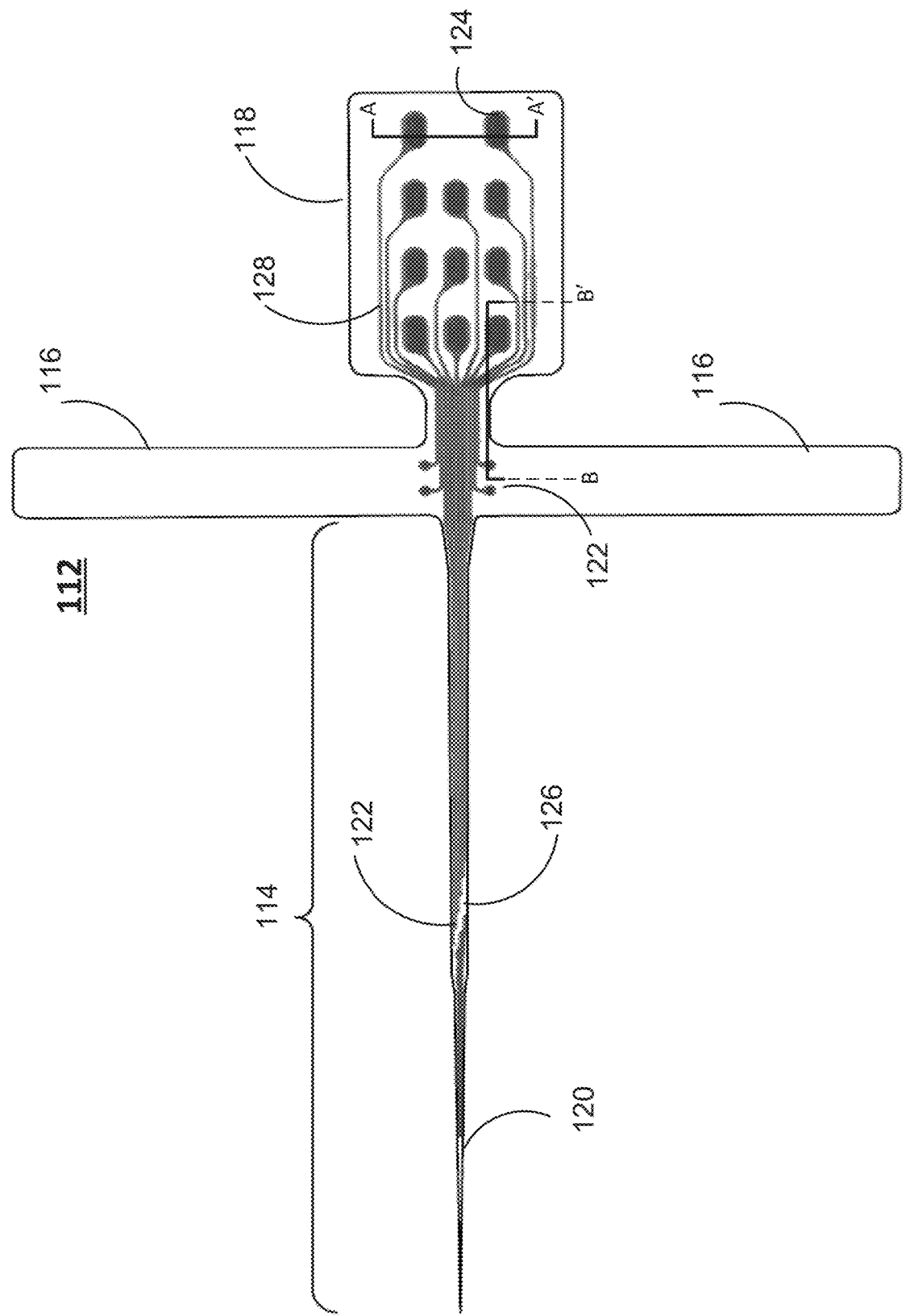
FIG. 2 illustrates a top view of an example electrode for use in the system illustrated in FIG. 1.

FIG. 2 illustrates a top view of an example electrode 112. The electrode 112 includes a rostrum 114, a tab 116 projecting from the central body of the electrode 112, and a connector pad 118. The rostrum 114 includes a needle 120 and a plurality of electrode sites 122. The tabs 116 also include a plurality of electrode sites 122. The connector pad 118 includes a plurality of contact pads 124.

As described in relation to FIG. 4A-4K, the electrode 112 is a multi-layer device that includes one or more metal layers sandwiched between silicone layers. The electrode sites 122, the traces 128, and the contact pads 124 are formed from the metal layer. The silicone layers insulate the metal layer and form the body of the electrode 112.

The rostrum 114 of the electrode 112 includes the needle 120 and a plurality of electrode sites 122. In some implementations, the tabs 116 also include electrode sites 122. The rostrum 114 is configured for insertion into nervous tissue, such as a peripheral nerve. The needle 120 enables the rostrum 114 to be threaded through a nerve fascicle or other tissue. In some implementations, the needle 120 is manufactured from a material that does not substantially bend when inserted into a target tissue. The needle 120 can be substantially rigid while the rest of the electrode 112 is substantially flexible. The needle 120 can include stainless steel, platinum, or another medical grade metal. The needle 120 is detachable from the remainder of the rostrum 114 and electrode 112. For example, a gap 126 in the metal layer between the electrode sites 122 and the needle 120 is manufactured in the rostrum 114. The gap 126 can include materials, such as the silicone layers, that are easy to cut. After threading the rostrum 114 into the patient's nerve fascicle, a surgeon may use surgical scissors to cut through the gap 126 and sever the needle 120 from the electrode 112. In some implementations, the needle 120 had an outer diameter between about 75 µm and about 200 µm, between about 100 µm and about 175 µm, or between about 125 µm and about 150 µm.

The rostrum 114 also includes a plurality of electrode sites 122. The electrode sites 122 are disposed on the rostrum 114 towards the ends of the traces 128. In some implementations, each electrode site 122 is an exposed area of the trace 128. For example, the trace 128 is a portion of a metal layer encapsulated within the silicone layers. A portion of the silicone layer above the trace 128 can be laser ablated to expose a portion of the metal layer—forming the electrode site 122. In some implementations, each of the electrode sites 122 are spaced between about 100 µm and about 700 µm, between about 200 µm and about 600 µm, or between about 300 µm and about 500 µm apart along the rostrum's length. In some implementations, each of the electrode site 122 have a diameter between about 50 µm and about 300 µm, between about 50 µm and about 200 µm, or between about 50 µm and about 100 µm.

Each of the traces 128 terminate at a contact pad 124 on the connector pad 118. In some implementations, each of the traces 128 terminate at a different contact pad 124, making each of the electrode sites 122 individually addressable. In other implementations, one or more of the traces 128 terminate at the same contact pad 124. Wires of a flexible cable are welded to each of the contact pads 124 to couple the electrode 112 to the satellite 106. In some implementations, each of the contact pads 124 have a length between about 200 µm and about 500 µm, between about 200 µm and about 400 µm, or between about 200 µm and about 300 µm.

The tabs 116 are used to secure the electrode 112 to the nerve fascicle or other target site. The tabs 116 are flexible and include one or more layers of silicone. In some implementations, additional electrode sites 122 are distributed along the length of the tabs 116. The tabs 116 are configured to wrap around the nerve fascicle. Once wrapped around the nerve fascicle the tabs 116 can be coupled together to secure the electrode 112 to the nerve fascicle. For example, the ends of the tabs 116 can be sutured together to secure the electrode 112 to the nerve fascicle without having to suture directly to the nerve fascicle.

Figure 3:
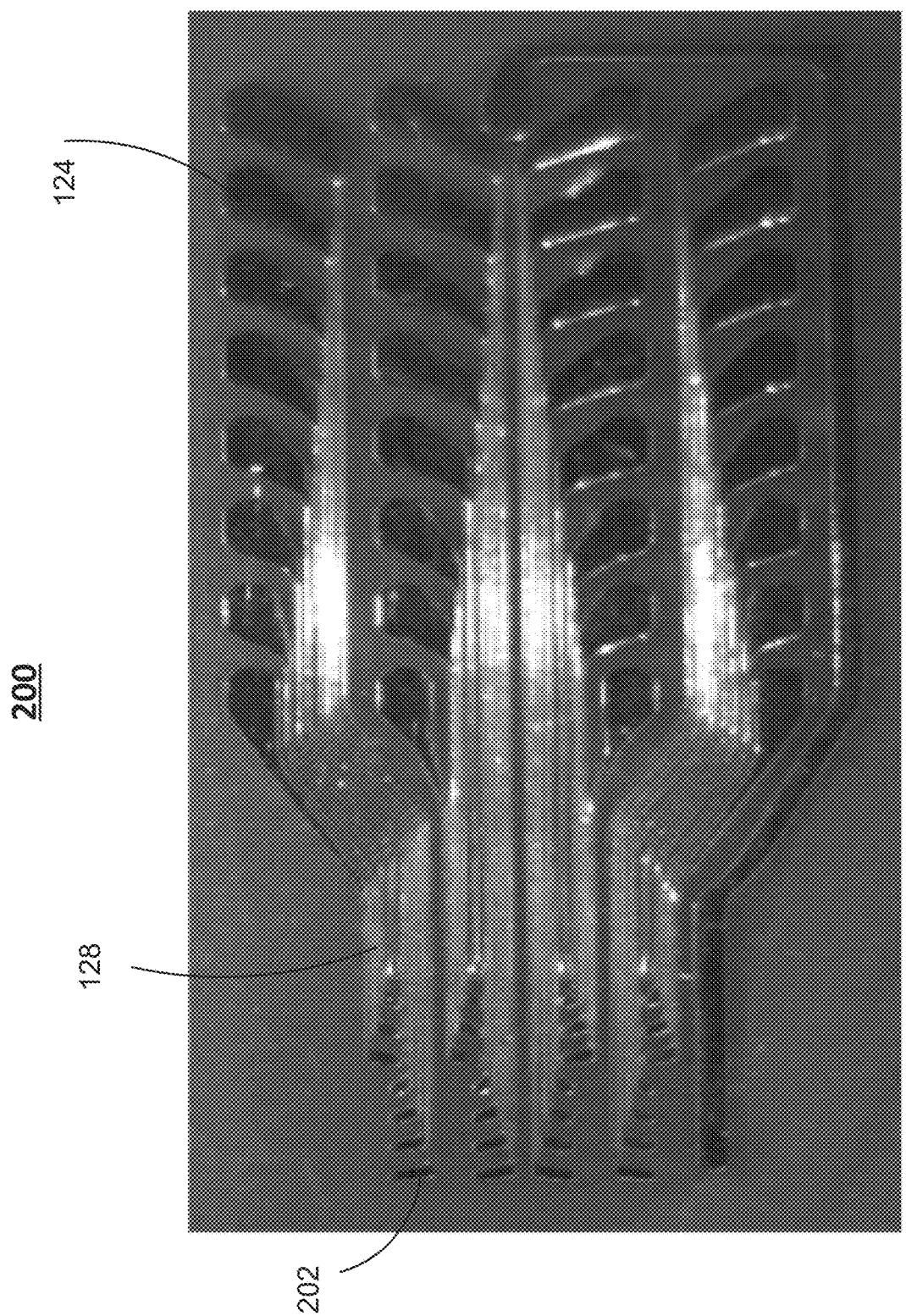
FIG. 3 illustrates another example electrode for use with the system illustrated in FIG. 1.

FIG. 3 illustrates another example electrode 200 for use with the system 100 discussed above. The electrode 200 is configured for electrocorticographic (ECoG) recordings. In this configuration the electrode 200 is configured for placement on the cortical tissue of a patient's brain to record (or stimulate) populations of cortical neurons. As illustrated, the electrode 200 includes 32 electrode sites 202. Each of the electrode sites 202 are coupled by traces 128 to a different contact pad 124. In some implementations, the electrode 200 includes between about 2 and about 128, between about 2 and about 64, or between about 2 and 32 electrode sites 202.

The electrode sites 202 of the electrode 200 are configured to have greater relative surface area compared to the electrode sites 122 discussed above. For example, the larger surface area enables the electrode sites 202 to receive electrical signals form a greater number of neurons.

Figure 4A:
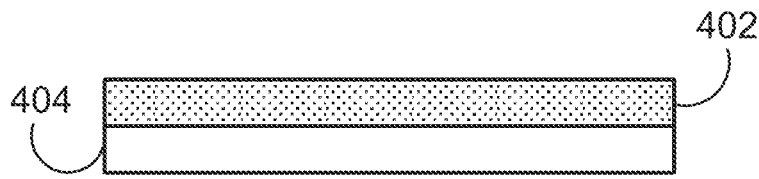
FIGS. 4A-4K illustrate cross-sectional views of a method for manufacturing an example electrode for use with the system illustrated in FIG. 1.

FIGS. 4A-4K illustrate cross-sectional views of a method for manufacturing the electrodes described herein. The cross-sectional views are taken along the line A-A' shown in FIG. 2. FIG. 4A illustrates a cross-sectional view of the first step in manufacturing the electrodes described herein. In the first step, a metal layer 402 is applied to a release tape 404. In some implementations, the metal layer 402 includes stainless steel or a platinum iridium alloy. In some implementations, the metal layer 402 may be a metal foil that is between about 10 µm and about 30 µm, between about 10 µm and about 15 µm, or between about 10 µm and about 12.5 µm thick. In some implementations, the release tape 404 is a thermal release tape or a UV release tape. In other implementations, the release tape 204 can be dissolved using a solvent.

Figure 4B:
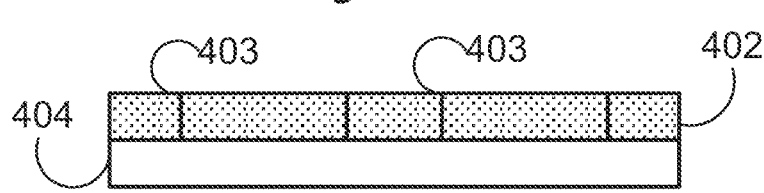

FIG. 4B illustrates a cross-sectional view of the electrode during the second stage of the manufacturing process. The metal layer 402 is cut to form the electrode sites, traces, contact pads of the electrode, and any other element of the metal layer. Laser ablation is used to form cuts 403 in the metal layer or metal foil 402. In some implementations, the laser may be a picosecond pulsed laser operating at a wavelength between about 245 nanometers and about— 2000 nanometers and configured with a pulse width between about 40 picoseconds and about 500 picoseconds. In other implementations, the laser may be a nanosecond pulsed laser and/or a femtosecond pulsed laser.

Figure 4C:
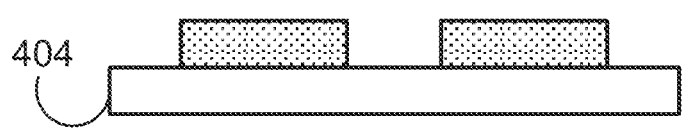

FIG. 4C illustrates a cross-sectional view of the electrode after the excess metal is removed from the release tape 404. The relatively larger portions of the metal layer 402 that do not form a portion of the electrode sites, traces, and contact pads can be peeled off from the release tape 404 to leave just the desired portions of the portions of the metal layer 402 forming the electrode sites, traces, and contract pads coupled to the release tape 404. In other implementations, relatively smaller portions of the metal layer 402 are entirely removed through laser ablation. For example, the portion of the metal layer 402 between two neighboring traces may be removed through laser ablation. After removing the release tape 404 from the metal layer 402, the remaining metal is cleaned using pure oxygen plasma to remove any residual organic material and to improve adhesion to the silicone layer described in FIG. 4D.

Figure 4D:

FIG. 4D illustrates a cross-sectional view of a first silicone layer 406 that is formed separately from the metal layer 402 and the release tape 404. The first silicone layer 406 may include an implantable grade silicone substrate specifically designed for implantation within the body of a human or an animal. The first silicone layer 406 may include a nylon, polyamide, polyester mesh. The mesh is impregnated with liquid silicone, which is then cured, to form the first silicone layer 406. In some implementations, the first silicone layer 406 is formed by knife-coating the mesh with uncured silicone, for example MED 4850 or MED 4250 silicone manufactured by NuSil™ of Carpinteria, CA In some implementations, the mesh is a MEDIFAB® mesh (part number 07-64/45) made available by SEFAR AG of Thal, Switzerland. In some implementations, the mesh is between about 40 µm and about 50 µm thick. In other implementations, the mesh is about 75 µm thick. The mesh can include an open area of between about 40% and about 50%. In some implementations, the diameter of each mesh fiber is between about 30 µm and about 50 µm and the fibers are spaced between about 60 µm and about 70 µm apart. For example, the mesh can be knife-coated with silicone, which is then cured, and then, additionally, or alternatively, be calendared (e.g., heat pressed) to achieve a desired thickness. The mesh can reinforce the first silicone layer 406 to improve the longevity of the electrode, ease the handling of the electrode, and provide structural integrity to the electrode. In some implementations, the improved structural integrity of the first silicone layer 406 reduces the likelihood that the metal layer 402 will separate from the first silicone layer 406 in subsequent steps or during the handling of the completed electrode. In some implementations, the first silicone layer 406 is between about 50 µm and about 100 µm, between about 60 µm and about 90 µm, or between about 70 µm and about 80 µm thick.

Figure 4E:

FIG. 4E illustrates a cross-sectional view of the next step in manufacturing the electrodes described herein. In this step, a glue layer 408 is applied to the first silicone substrate 406. The glue layer 408 is applied to the top surface of the first silicone layer 406 to help hold the additional layers of material to the first silicone layer 406.

Figure 4F:
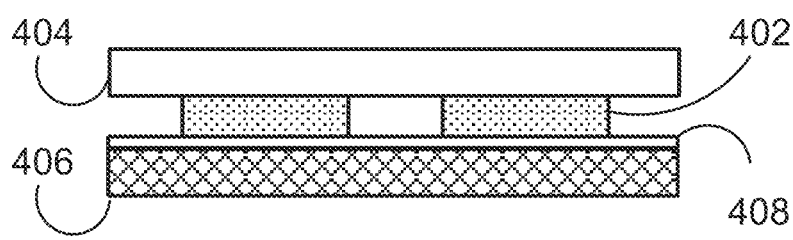

FIG. 4F illustrates a cross-sectional view of the sixth step in manufacturing the electrodes described herein. As illustrated in FIG. 4F, the metal layer 402 and release tape 404 (from FIG. 4C) are inverted and coupled to the glue layer 408 (from FIG. 4E). The glue layer 408 is then cured to permanently fix the metal layer 402 to the first silicone layer 406.

Figure 4G:
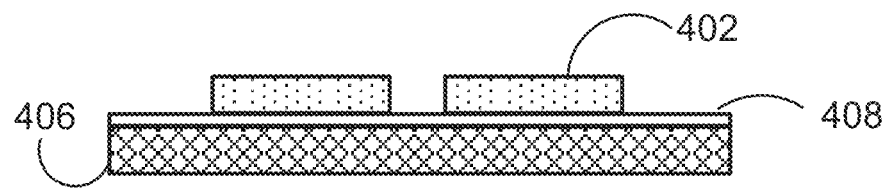

FIG. 4G illustrates a cross-sectional view of the seventh step in manufacturing the electrodes described herein. Once the metal layer 402 is coupled to the glue layer 408, the release tape 404 is removed from the metal layer 402. In some implementations, the release tape 404 is removed by heating the release tape 404 to a predetermined temperature, which causes the release tape 404 to release (or dissolve) from the metal layer 402. In other implementations, the release tape 404 can be dissolved with a solvent or exposed to UV light to cause the release tape 404 to release from the metal layer 402.

Figure 4H:
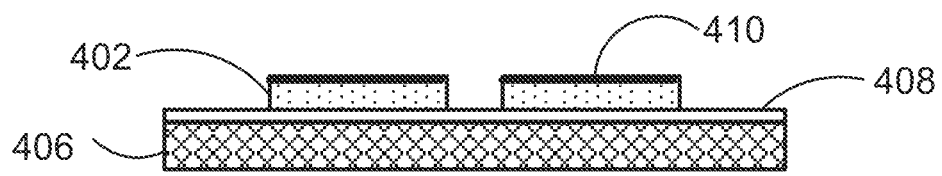

FIG. 4H illustrates the next step in manufacturing the electrodes described herein. Once the release tape 404 is removed, the exposed metal layer 402 is cleaned using oxygen plasma and a primer 410 is applied to the exposed metal layer 402. For example, a silicone primer such as MED6-161 manufactured by NuSil™ of Carpinteria, CA may be used to increase the adhesion of the metal layer 402 to a second layer of silicone.

Figure 4I:
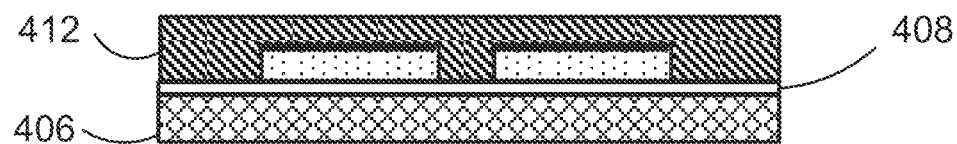

FIG. 4I illustrates a cross-sectional view of the ninth stage of manufacturing the electrodes described herein. Once the primer 410 has been applied to the exposed metal layer 402, the metal layer 402 is encapsulated with a second silicone layer 412. The second silicone layer 412 may include a calendared layer of silicone. For example, the second silicone layer 412 may be produced by calendaring or applying heat and mechanical force to create the second silicone layer 412 at a desired thickness. Using this technique, the second silicone layer 412 may be as thin as 50 µm. In some implementations, the second silicone layer 412 is between about 50 µm and 100 µm thick. In other implementations, the second silicone layer 412 is similar to the first silicone layer 406. For example, the second silicone layer 412 can be impregnated with a mesh. In other implementations, the second silicone layer 412 is not impregnated with a mesh, but may be about the same thickness as the first silicone layer 406.

Figure 4J:
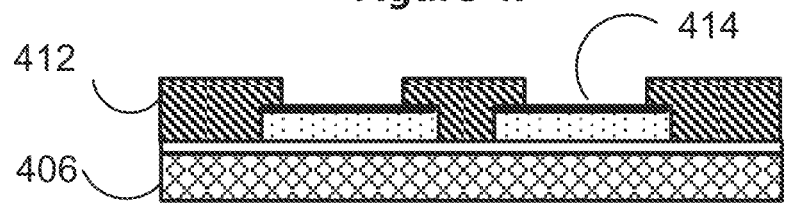

FIG. 4J illustrates a cross-sectional view of the tenth stage of manufacturing the electrodes described herein. Once the metal layer is encapsulated with the second silicone layer 412, one or more sets of holes or openings 414 are formed in the second silicone layer 412. The sets of holes 414 expose a portion of the metal layer 402. The openings or sets of holes 414 are formed over the portions of the metal layer 402 that form electrode sites and the contact pads. The openings 414 may be created using laser ablation. After the sets of holes or openings 414 have been created, the exposed metal layer is cleaned using oxygen plasma mixed with tetrafluoromethane gas to remove any residual silicone that may remain on the contact pads or electrode sites following the laser ablation. In some implementations, a thin layer of silicone is intentionally left in the openings 414 (e.g., the openings over the contact pads and/or the electrode sites) prior to the aforementioned cleaning process to prevent the laser from damaging the contact pads or electrode sites. In some implementations, the electrode sites may be located on the same side of the electrode as the contact pads. In some implementations, the electrode sites may be located on the opposite side of the electrode as the contact pads.

In some implementations, the first and second silicone layers 406 and 412 are larger than the total shape of the electrode. For example, the metal layer 402 defining a plurality of electrodes can be laminated between large, single first and second silicone layers 406 and 412. In these implementations, after forming the sets of holes or openings 414 for each respective electrode site and contact pad, each of the electrodes are cut from the first silicone layer 406 and the second silicone layer 412 by laser cutting the shape of each electrode body from the first silicone layer 406 and the second silicone layer 412. The edges of the formed electrodes may be cleaned by plasma cleaning.

Figure 4K:
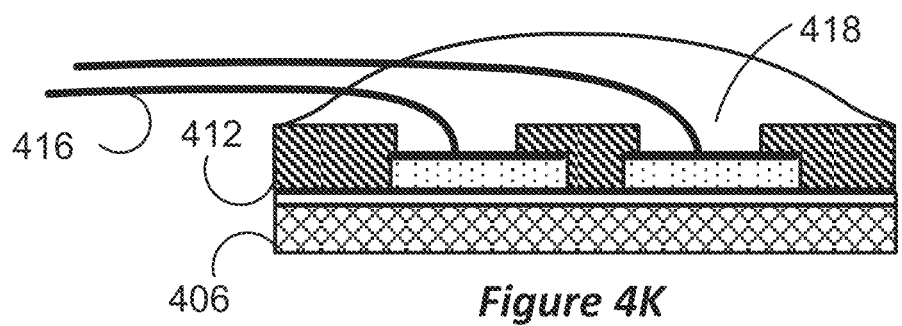

FIG. 4K illustrates a cross-sectional view of the next stage of manufacturing the electrodes described herein. As shown in FIG. 4K, where the openings 414 are formed over the contact pads, the wires 416 are coupled to each of the exposed metal areas that form the contact pads. The wires 416 are welded to the exposed metal layer 402. In some implementations, the wires are resistance welded to the exposed metal layer 402. In other implementations, the wires are laser welded to the exposed metal layer 402. The wires 416 couple the contact pads (and ultimately, the electrode sites) to the satellites described above. To protect the weld between the wires 416 and metal layer 402 (e.g., at the location of each contact pad), a third silicone layer 418 is applied as an overmold over the openings 414, (e.g., the one or more contact pad openings). The openings that are formed over the electrode sites are not covered with the third silicone layer, e.g., the overmold 418, so that the metal layer is exposed and can record and stimulate the neural tissue. The third silicone layer 418 is overmolded onto the first or second silicone layer to achieve a gradual transition between the first or second silicone layer and the third silicone layer. The gradual transition between the first or second silicone layer and the third silicone layer is substantially smooth, for example, such that is does not possess sharp angles, abrupt changes and/or discontinuities in the gradient of the slope of the overmolded third silicone layer.

In some implementations, such for the manufacture of an intra-fascicular electrode similar to the electrode 112 illustrated in FIGS. 1 and 2, the manufacturing method illustrated in FIGS. 4A-4K continues with the coupling of a needle to the electrode's formed body. In some implementations, such as when the electrode is configured for cortical recordings and stimulation, the electrode does not include a needle and the manufacturing method ends at the step illustrated in FIG. 4K. In some implementations, the needle is coupled to the electrode with a biocompatible glue. In some implementations, the transition between the needle and the electrode is configured to be substantially smooth such that the transition does not cause damage when the rostrum is pulled through a nerve fascicle. In some implementations, the end of the needle coupled to the electrode is first thinned, such that the combination of the needle material and the electrode does not form a bulge along the electrode's rostrum. The needle can be thinned by grinding down a portion of the needle.

FIGS. 5A-5D illustrate cross-sectional views of example electrodes manufactured by the method illustrated in FIGS. 4A-4K. The cross-sectional views are taken along the line B-B' shown in FIG. 2. A variety of electrode shapes and formations may be enabled by this method of manufacturing. For example, the method of manufacture described herein may be used, but is not limited to, the manufacture of electrocorticographic (ECoG) electrodes, micro-electrocorticographic electrodes, longitudinal intra-fascicular electrodes, cuff electrodes, transverse intra-fascicular electrodes, and surface electrodes. The arrangement of electrode sites and contact pads may vary based on the nerve size, nerve location or area of nerve tissue to be stimulated or from which signals are to be recorded. A larger electrode surface area may include more electrode sites enabling the electrode to receive electrical signals form a greater number of neurons. For example, an electrode may be configured for electrocorticographic (ECoG) recordings. The electrode may be placed on the cortical tissue of a patient's brain to record (or stimulate) populations of cortical neurons. The electrode may include between about 2 and about 128, between about 2 and about 64, or between about 2 and 32 electrode sites. In some implementations, each of the electrode sites 122 are spaced between about 100 µm and about 700 µm, between about 200 µm and about 600 µm, or between about 300 µm and about 500 µm apart from each other.

The arrangement of the contact pads and traces connecting the electrode site to the contact pad may also vary. In some implementations, each of the traces terminates at a contact pad corresponding to a specific electrode site, making each of the electrode sites individually addressable. In other implementations, each of the traces terminates at a different contact pad. In some implementations, one or more of the traces terminate at the same contact pad. In some implementations, each of the contact pads has a length between about 200 µm and about 500 µm, between about 200 µm and about 400 µm, or between about 200 µm and about 300 µm.

Figure 5A:
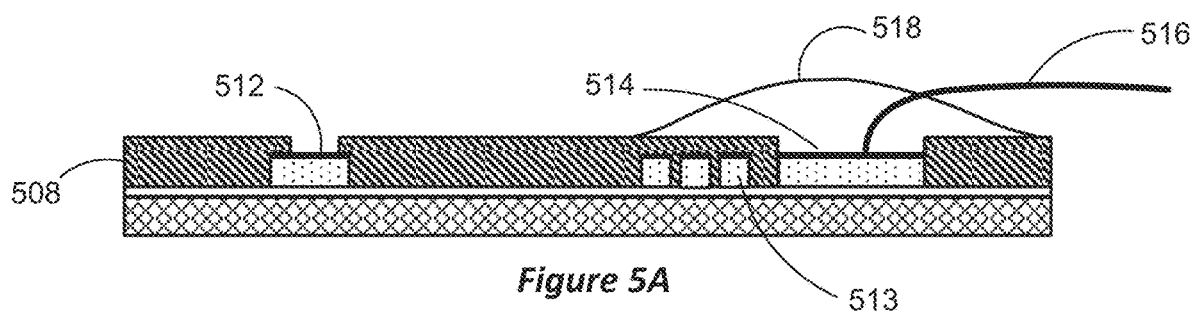
FIGS. 5A-5D illustrate cross-sectional views of example electrodes manufactured by the method illustrated in FIGS. 4A-4K

FIG. 5A illustrates a cross-sectional view of an electrode where the electrode site opening 512 and the contact pad opening 514 are formed on the same side of the electrode. As shown in FIG. 5A, the electrode site opening 512 and the contact pad opening 514 are formed in the second silicone layer 508. One or more traces 513 connect the electrode site to the contact pad. A wire 516 is welded to the contact pad and an overmold 518 is applied over the contact pad opening 514.

Figure 5B:
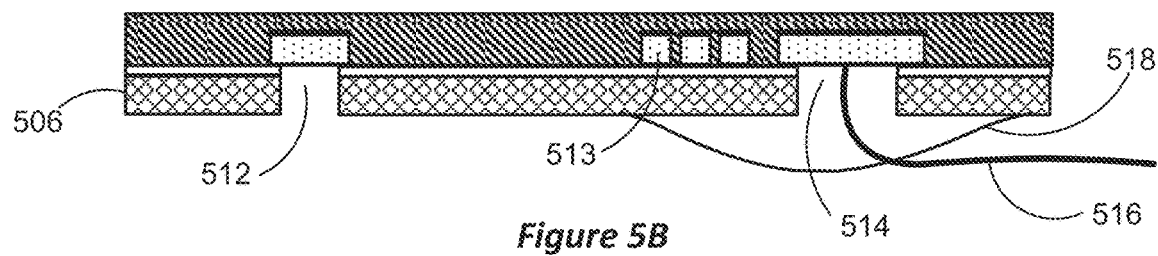

FIG. 5B illustrates a cross-sectional view of an electrode where the electrode site opening 512 and the contact pad opening 514 are also formed on the same side of the electrode. As shown in FIG. 5B, the electrode site opening 512 and the contact pad opening 514 are formed in the second silicone layer 506. One or more traces 513 connect the electrode site to the contact pad. A wire 516 is welded to the contact pad and an overmold 518 is applied over the contact pad opening 514.

Figure 5C:
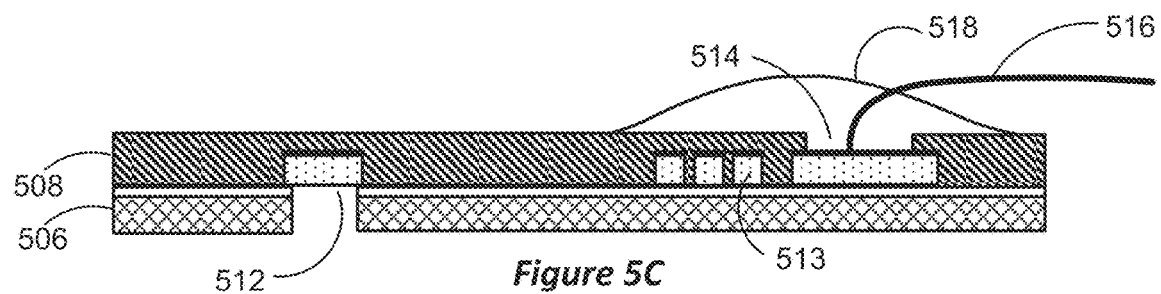

FIG. 5C illustrates a cross-sectional view of an electrode where the electrode site opening 512 and the contact pad opening 514 are formed on opposite sides of the electrode. As shown in FIG. 5C, the electrode site opening 512 is formed in the first silicone layer 506 and the contact pad opening 514 is formed in the second silicone layer 508. One or more traces 513 connect the electrode site to the contact pad. A wire 516 is welded to the contact pad and an overmold 518 is applied over the contact pad opening 514.

Figure 5D:
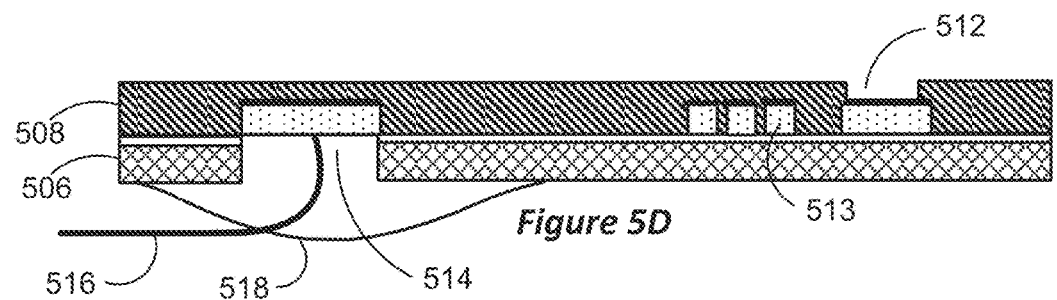

FIG. 5D illustrates a cross-sectional view of an electrode where the electrode site opening 512 and the contact pad opening 514 are also formed on opposite sides of the electrode. As shown in FIG. 5D, the electrode site opening 512 is formed in the second silicone layer 508 and the contact pad opening 514 is formed in the first silicone layer 506. One or more traces 513 connect the electrode site to the contact pad. A wire 516 is welded to the contact pad and an overmold 518 is applied over the contact pad opening 514.

Figure 6:
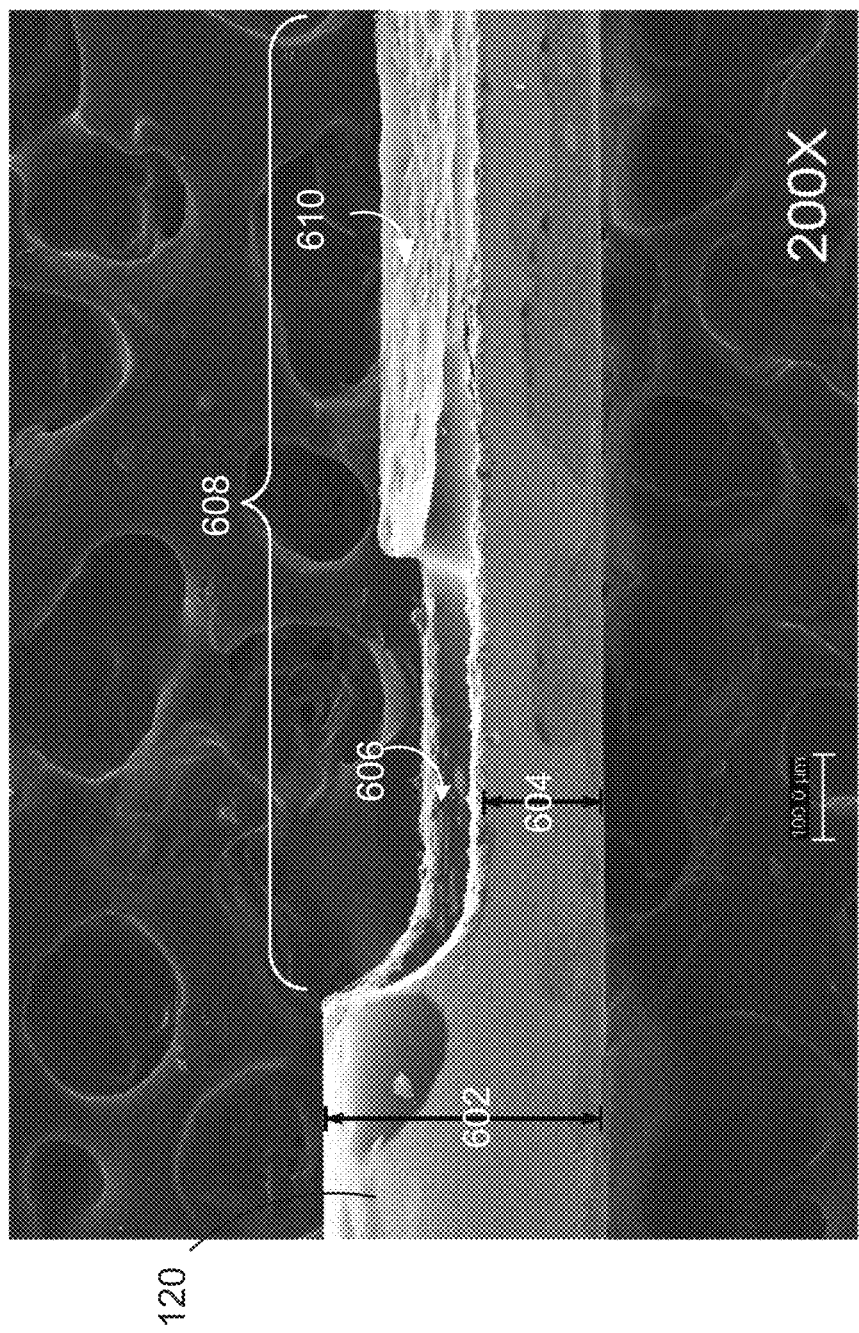
FIG. 6 illustrates a scanning electron micrograph of the coupling of the needle to an electrode for use with the system illustrated in FIG. 1.

FIG. 6 illustrates a scanning electron micrograph of the coupling between the needle and the electrode formed using the above described manufacturing method. FIG. 6 illustrates that the needle 120 is thinned from its initial thickness 602 to a thinned thickness 604 that is about half the thickness of the initial thickness 602. In the example illustrated in FIG. 6, the initial thickness 602 is about 350 µm and the thinned thickness 604 is about 175 µm. Thinning the needle 120 exposes the needle's inner lumen 606 and forms a trough 608. The portion 610 of the rostrum 114 that couples to the needle 120 is sized to fit into the trough 608. The portion 610 can then be glued to the trough 608.

The disclosed methods may be embodied in other specific forms without departing from the spirit or essential characteristics thereof. The forgoing implementations are therefore to be considered in all respects illustrative, rather than limiting of the invention.

What is claimed:

1. A method of manufacturing an implantable neural electrode comprising:
    cutting a metal layer to form a plurality of electrode sites, contact pads and metal traces, wherein the metal layer is about 5 µm to 25 µm thick and wherein the metal traces connect one or more electrode sites to one or more contact pads;
    forming a first silicone layer by:
        knife-coating a polymer mesh with silicone, such that the first silicone layer has a thickness between about 50 µm and about 100 µm, and
        curing the first silicone layer;
    coupling the metal layer to the first silicone layer;
    forming a second silicone layer by calendaring silicone to a thickness between about 50 µm and about 100 µm;
    laminating the first silicone layer to the second silicone layer such that the metal layer is positioned between the first silicone layer and the second silicone layer;
    forming a first set of holes in the first or second silicone layers to expose one or more electrode sites and a second set of holes in the first or second silicone layers to expose one or more contact pads in the metal layer;
    after exposing the one or more contact pads, welding one or more wires to the one or more exposed contact pads; and
    overmolding a third silicone layer over the one or more welded contact pads and a portion of the wires.

2. The method of claim 1, further comprising applying a release tape to the metal layer prior to cutting the metal layer.

3. The method of claim 2, further comprising removing the release tape from the metal layer after coupling the cut metal layer to the first silicone layer.

4. The method of claim 3, wherein removing the release tape comprises one of heating the release tape, dissolving the release tape with a solvent and exposing the release tape to ultraviolet light.

5. The method of claim 1, wherein prior to laminating the first silicone layer to the second silicone layer the method further comprises cleaning the metal layer with oxygen plasma.

6. The method of claim 5, wherein after cleaning the metal layer with oxygen plasma the method further comprises depositing a primer on the metal layer.

7. The method of claim 1, wherein forming the first silicone layer comprises knife-coating the mesh such that the first silicone layer is between about 60 µm and about 90 µm thick and forming the second silicone layer comprises calendaring the second layer of silicone to be between about 60 µm and about 90 µm thick.

8. The method of claim 1, wherein forming the first silicone layer comprises knife-coating the mesh such that the first silicone layer is between about 70 µm and about 80 µm thick and forming the second silicone layer comprises calendaring the second silicone layer to be between about 70 µm and about 80 µm thick.

9. The method of claim 1, further comprising cutting the metal layer and forming the first set of holes and the second set of holes in the first or second silicone layers using laser ablation.

10. The method of claim 9, wherein the laser ablation comprises using a picosecond pulsed laser.

11. The method of claim 1, wherein the mesh comprises nylon, polyamide or polyester fibers.

12. The method of claim 11, wherein the mesh includes an open area comprising between 40% and 50% of the total area of the mesh.

13. The mesh of claim 11, wherein each fiber comprises a diameter between about 30 µm and about 50 µm.

14. The mesh of claim 11, wherein the fibers are spaced about 60 µm and about 70 µm apart.

15. The method of claim 11, wherein the mesh is between about 40 μm and about 50 μm thick.

16. The method of claim 1, wherein welding comprises resistance welding or laser welding.

17. The method of claim 1, wherein the third silicone layer is overmolded onto the second silicone layer, and the overmolding achieves a gradual transition between the second silicone layer and the third silicone layer.

18. The method of claim 1, wherein the third silicone layer is overmolded onto the first silicone layer, and the overmolding achieves a gradual transition between the first silicone layer and the third silicone layer.

19. The method of claim 1, wherein the first set of holes and the second set of holes are both formed in the first layer of silicone or are both formed in the second layer of silicone.

20. The method of claim 1, wherein the first set of holes are formed in a different layer of silicone than the layer of silicone in which the second set of holes are formed.

* * * * *